United States Patent [19]

Kronwald

[11] Patent Number: 4,888,112
[45] Date of Patent: Dec. 19, 1989

[54] CHROMATOGRAPHIC COLUMN

[75] Inventor: Klaus Kronwald, Sinsheim, Fed. Rep. of Germany

[73] Assignee: Labomatic GmbH, Sinsheim, Fed. Rep. of Germany

[21] Appl. No.: 332,396

[22] Filed: Mar. 28, 1989

Related U.S. Application Data

[63] Continuation of Ser. No. 116,882, Nov. 5, 1987, abandoned.

[30] Foreign Application Priority Data

Nov. 6, 1986 [DE] Fed. Rep. of Germany ....... 3637916

[51] Int. Cl.4 ............................................. B01D 15/08
[52] U.S. Cl. .................................. 210/198.2; 210/94; 210/450; 55/386
[58] Field of Search ................ 210/94, 95, 198.2, 450, 210/656, 659; 55/386

[56] References Cited

U.S. PATENT DOCUMENTS

| 3,474,908 | 10/1969 | Catravas | 210/198.2 |
| 3,483,986 | 12/1969 | Wright | 210/198.2 |
| 3,487,938 | 1/1970 | Patterson | 210/198.2 |
| 3,511,377 | 5/1970 | Hrdina | 55/386 |
| 3,791,522 | 2/1974 | Eisenbeiss | 210/198.2 |
| 3,878,099 | 4/1975 | Ogle | 210/198.2 |
| 3,954,291 | 5/1976 | Gunner | 285/341 |
| 4,168,235 | 9/1979 | Guillemin | 210/198.2 |
| 4,280,905 | 7/1981 | Gunkel | 210/198.2 |
| 4,289,620 | 9/1981 | Hara | 210/198.2 |
| 4,350,595 | 9/1982 | Gunkel | 210/198.2 |
| 4,361,482 | 11/1982 | Teetz | 210/198.2 |
| 4,451,365 | 5/1984 | Sattler | 210/198.2 |
| 4,636,315 | 1/1987 | Allen | 210/198.2 |
| 4,692,243 | 9/1987 | Porsch | 210/198.2 |
| 4,737,284 | 4/1988 | Hauke | 210/198.2 |

FOREIGN PATENT DOCUMENTS

| 0023582 | 7/1980 | European Pat. Off. | 210/198.2 |
| 0068343 | 6/1982 | European Pat. Off. | 210/198.2 |
| 0131791 | 6/1984 | European Pat. Off. | 210/198.2 |
| 1278401 | 10/1903 | Fed. Rep. of Germany | 210/198.2 |
| 2132686 | 1/1973 | Fed. Rep. of Germany | 210/198.2 |
| 2348071 | 9/1975 | Fed. Rep. of Germany | 210/198.2 |
| 2945180 | 5/1980 | Fed. Rep. of Germany | 210/198.2 |
| 8629692 | 8/1982 | Fed. Rep. of Germany | 210/198.2 |
| 509591 | 8/1970 | Switzerland | 210/198.2 |
| 868586 | 9/1981 | U.S.S.R. | 210/198.2 |

OTHER PUBLICATIONS

"BDH Product Information", Merck Lobar prepacked columns for liquid chromatography, 1977.
Merck Prospekt: Lobar Fertigsaulen fur die Flussigkeitschromatographie, 1977, pp. 2 and 3.

Primary Examiner—Ernest G. Therkorn
Attorney, Agent, or Firm—Foley & Lardner, Schwartz, Jeffery, Schwaab, Mack, Blumenthal & Evans

[57] ABSTRACT

The present invention relates to a chromtographic column having a tube, preferably made of glass, with sealed-off connection pieces, preferably with frets, the tube having at each end flanges, which together with a screw joint, connect the connection pieces to the tube. The connection pieces have a central tube which possesses a clamping ring above the fret recess at its end. The clamping ring is preferably of conical design and the tube is surrounded by a sleeve which acts on the clamping ring through a counterpiece, preferably an oppositely sloped cone. Arranged between the clamping surfaces is a squeezable seal. The sleeve is supported by the screw joint and the tube has a thread passing through the screw joint and can be fixed by a nut on the upper part of the screw joint.

16 Claims, 5 Drawing Sheets

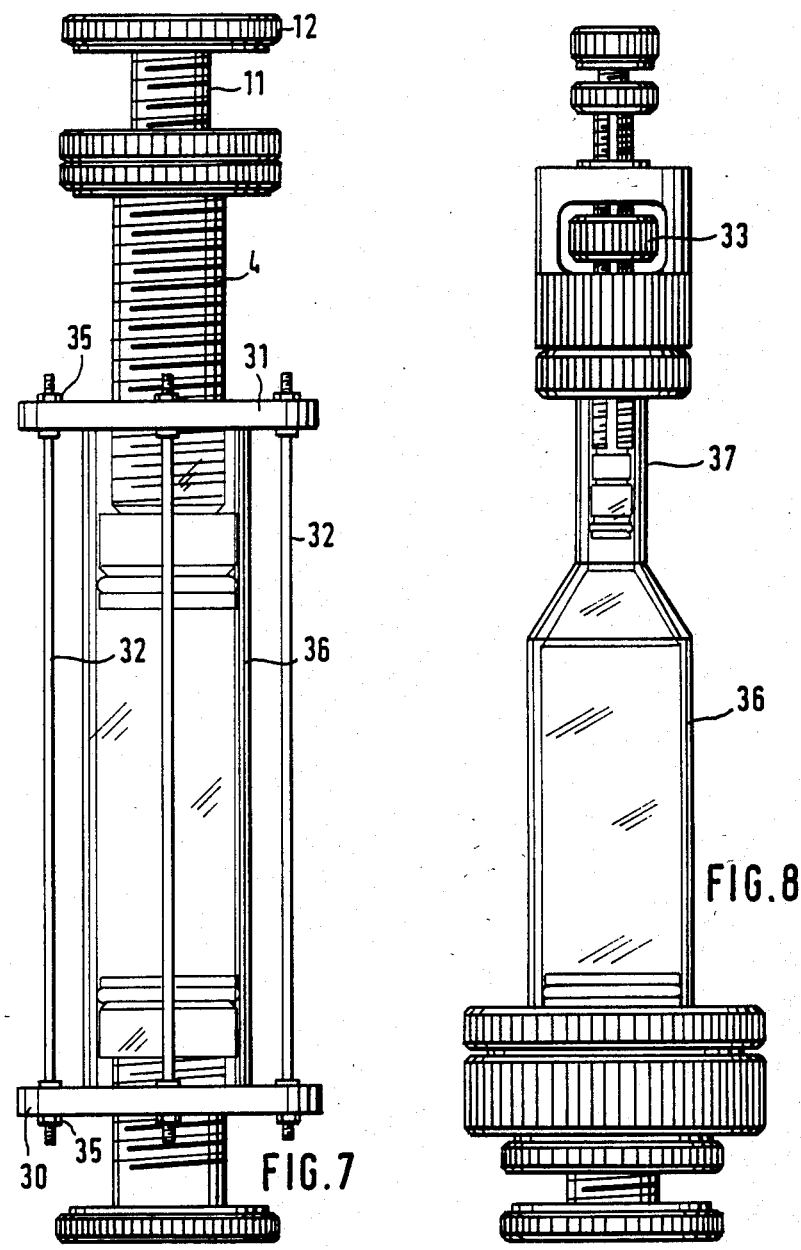

4,888,112

CHROMATOGRAPHIC COLUMN

This application is a continuation Ser. No. 116,882, filed Nov. 5, 1987, now abandoned.

BACKGROUND OF THE INVENTION

The present invention relates to a chromatographic column.

Chromatographic columns are used for the separation of substance mixtures and are based on the use of the property of gases or liquids existing in specific sorption coefficients which manifest themselves in differing retention times. Of essential importance for a clear cut separation is the behavior of the liquids passing through the column. Since chromatographic separations are often carried out under pressure and changes in bed volume arise due to this pressure and other factors, inhomogeneities in the bed or between the bed and the upper part of the bed and the feed in the form of dead volume result, impairing a reproducible, straight front profile of the free-flowing media. Pressure losses have a similarly disturbing effect.

It is known to use seals in the form of rubber O-rings, which are laid on the upper rim of the column and squeezed by a cap screw joint, accommodating the supply and discharge lines, against the widened column ring bearing against the underside of the latter.

A disadvantage with the known chromatographic columns is that the nature of the screw joint does not allow a visual inspection either of the seal or of the transition of the liquid from the feed into the chromatographic bed, or of the liquid from the chromatographic bed into the feed.

Furthermore, the distance between bed surface and liquid feed cannot be satisfactorily bridged.

SUMMARY OF THE INVENTION

One object of the present invention is to provide a chromatographic column which makes it possible to view the transition zone between feed and bed and also to perform a visual inspection of the seal.

In accomplishing the foregoing objects, there has been provided according to the present invention an apparatus for connecting a chromatographic column to a liquid feed, the column having two axial ends and an inner surface, comprising a tube having an upper and lower part, the lower part having a frit recess for communicating with the interior of the column and having a clamping ring comprising a surface generally facing in one axial direction; a sleeve surrounding the tube, the sleeve having a counterpiece comprising a surface generally facing in the opposite axial direction; means for supporting the sleeve on the end of the column; means for axially moving the tube relative to the sleeve; and a squeezable seal disposed around the tube and contacting the clamping ring of the tube and the counterpiece of the sleeve, the seal being adapted to move radially outwardly when the tube is moved relative to the sleeve and the seal is squeezed between the clamping ring and the counterpiece, the seal sealingly engaging the inner surface of the column as it moves radially outwardly.

In another aspect of the present invention, there has been provided a chromatographic column, comprising a tube having an upper and lower part, the lower part having a frit recess for communicating with the interior of the column and having a clamping ring comprising a surface generally facing in one axial direction; a sleeve surrounding the tube, the sleeve having a counterpiece comprising a surface generally facing in the opposite axial direction; means for supporting the sleeve on the end of the column; means for axially moving the tube relative to the sleeve; and a squeezable seal disposed around the tube and contacting the clamping ring of the tube and the counterpiece of the sleeve, the seal being adapted to move radially outwardly when the tube is moved relative to the sleeve and the seal is squeezed between the clamping ring and the counterpiece, the seal sealingly engaging the inner surface of the column as it moves radially outwardly.

Further objects, features and advantages of the present invention will become apparent from the detailed description of preferred embodiments which follows, when considered together with the attached figures of drawing.

BRIEF DESCRIPTION OF THE DRAWINGS

The present invention is explained in more detail with reference to the enclosed figures.

FIG. 7 is a cross-sectional view of the safeguard with the aid of tie rods; and

FIG. 8 is a cross-sectional view of another embodiment of the invention having connections to an asymmetric column.

DETAILED DESCRIPTION OF THE PREFERRED EMBODIMENTS

Figure 1:
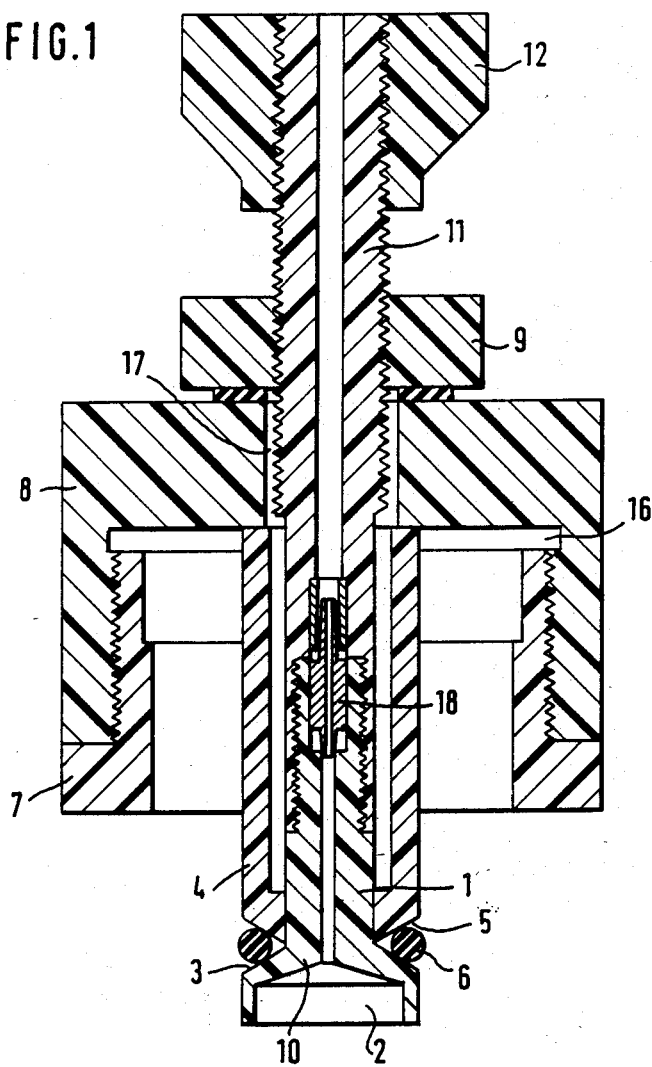
FIG. 1 is a longitudinal cross-sectional view of a column according to the invention, in section.

In a preferred embodiment of the invention, large dead zones between the feed and the bed can be bridged, i.e., the feed can be positioned precisely as a function of the particular prevailing pressure conditions and the bed volume.

A chromatographic column is provided consisting of a tube, preferably made of glass, with sealed-off connection pieces, preferably with frits, the tube having at each end flanges, with the aid of which the connection pieces can be connected to the tube with the aid of a screw joint. The column has the following features:

(a) the connection pieces have a central tube (1), which has a clamping ring above the frit recess (2) arranged at its end, which clamping ring is preferably of conical design (3);

(b) the tube (1) is surrounded by a sleeve (4), which acts on the clamping ring (3) through a counterpiece, preferably an oppositely sloped cone (5);

(c) a squeezable seal (6) is arranged between the clamping surfaces (3; 5);

(d) the sleeve (4) is supported by the screw joint (7; 8);

(e) the tube (1) has a thread passing through the screw joint and can be fixed by a nut (9) on the upper part of the screw joint (8).

In this apparatus, the seal is moved to inside the column and onto the bed, in the region of the feed of the mixture to be separated. Due to the squeezing device, the O-ring is acted on from three areas and is pushed away from the tube towards the glass jacket of the column and is thus in a position to bridge large production tolerances. This operation is supported by the clamping rings which preferably having conical surfaces.

Due to the positioning of the feed with the aid of the sleeve, which is also part of the sealing mechanism at the lower end, two effects can be achieved. On the one hand, the length of the sleeve can go beyond the screw joint and thus ensure the visual inspection of seal and feed. On the other hand, simple selection of the sleeve length now makes it possible to position the feed, i.e., the frit, at a precisely predeterminable distance from the top edge of the column, i.e., it can be matched to the bed.

Of significance for system tightness is not only the column sealing but also the sealing of the liquid feed into the screw joint, i.e., in the present case into the tube.

According to the invention, a particularly advantageous embodiment of a highly pressure-resistant feed consists of a split tube which has an inner screw joint and a hose connector, which can be clamped between the two parts, and which has the form, for example, of a cone, onto which the supply line is pushed, and which has a counter cone fitted on the outside, which is held by the screw joint of the split tube.

The present invention furthermore offers a simple and effective structure for vertical adjustment of the tube, or of its liquid discharge comprising a screw joint upper part and a sleeve with interacting threads, which allows them to project upwardly beyond the screw joint upper part and to support the nut on the sleeve, whereby the necessary tensile force for the squeeze seal is provided.

Another embodiment of the present invention consists of a sleeve which extends out into the clamping surface for the squeeze seal, which is located on a separate socket, the sleeve abutting against the seal from above and the lower part of the tube bearing the frit insert abutting against the seal from below. This can, of course, have the effect of reducing the sleeve diameter without undesirable deformations occurring in the (conical) clamping surfaces, and thus material which is preferably made of polytetrafluoroethyelene can be saved.

Furthermore, a sliding surface between socket and sleeve is produced, so that socket and squeeze seal can remain stationary when the sleeve turns.

For operation of the vertical adjustment and of the squeeze seal, both sleeve and tube, or its upper part, can be provided with handles, for example, in the form of knurled discs, which are fixed against rotation with respect to their corresponding threaded parts.

A satisfactory seal is provided by an O-ring of rubber, the thickness of which has to be adapted to the distance to be overcome between the clamping rings and the glass wall.

However, in a preferred embodiment, the present invention also allows the use of plastic lip seals having clamping surfaces (preferably of PTFE) of conical design, so that they compress an insert arranged between them, which bears the lips on the outside, in such a way that the lips are spread radially and applied firmly to the glass wall. In this arrangement, the lips are preferably inclined in a way known per se the angle to the longitudinal axis varying according to the clamping pressure.

It is further envisaged to combine an O-ring seal with a scraper ring, likewise preferably made of PTFE. This scraper ring has the shape of an outwardly widening sharp-edged crown, which likewise has a corresponding conical surface, and which, with the aid of the corresponding counter surface, can substantially change the diameter of the crown rim whereby the crown at the same time performs a sealing function.

As the columns according to the invention an be operated for pressures of up to over 50 bar, provision must be made for an adequate pressure safeguard to prevent the connection piece from slipping out. For instance, flanges located on the end edges of the column, under which the screw joint lower part engages, could act as such a safeguard.

It is also possible to design the screw joint upper part as a plate lying against the column and to connect the plate by tie rods, the connection pieces likewise being screwed by a thread into the inside of the column.

The present invention also offers a further advantage, in that a cooling jacket can be connected to the screw joint in a particularly simple way, for which purpose said joint is provided with outer sealing rings, which engage over the cooling jacket in a sealing manner. In this case there is also the possibility in principle of absorbing tensile forces via the cooling jacket.

In FIG. 1, the end connection of a chromatographic column to a liquid feed is shown, the particular construction of which allows it to be under elevated or high pressure. "Upper" and "lower" directions are with reference to FIG. 1 and it is to be understood that the column has an identical, oppositely facing end connection at its opposite axial end. Screw joint lower part 7 and upper part 8 are supported on end flanges 16 of a chromatographic column, which preferably consists of glass. The screw joint upper part 8 has a central bore 17 and through this bore 17 is a tube 1, via which the mixture to be separated is fed or, conversely, the separated components are removed.

This tube is preferably split into a tube upper part 11 and tube lower part 10, which can be screwed together, with a screw clip 18 being held in between. The liquid feed takes place via a plastic hose, which is pushed into the cavity of the tube upper part 11 and connected and secured with the aid of the hose clip 18.

The end of the tube lower part 10 facing the column bed is widened to a feed or frit recess 2. This widening has a clamping surface above it, which is cone 3.

The tube 1, at its upper part 11, has a thread passing through the bore 17 of the screw joint upper part 8, on which thread a (knurled) nut 9 is arranged. At the top of tube 1 is a handle 12.

Arranged coaxially to, and surrounding, the tube 1 is a sleeve 4 which terminates at its downward end in a clamping surface comprising cone 5, which abuts against the cone 3 of the tube lower part 10. Between the cones 3 and 5 there is a squeeze seal in the form of rubber O-ring 6.

The sleeve 4 abuts at its opposite end against the underside of the screw joint upper part 8. By tightening the nut 9, the tube 1 is raised and at the same time the sleeve 4 pressed against the screw joint upper part 8. As a result, the cones 3 and 5 move toward each other and squeeze the O-ring outwardly against the column inner wall.

The length of the sleeve 4 is dimensioned such that seal 6 and frit recess 2 lie undeneath the screw joint lower part 7, so that a satisfactory visual inspection of the flowing medium is possible and inhomogeneities and/or leaks can be detected immediately.

In another preferred embodiment, the distance between screw joints 7, 8 and the upper edge of the column bed is designed to be variable, so that the distance can be optimized. For this purpose, the sleeve 4 has its own thread engaged with a corresponding thread of the screw joint upper part, the sleeve 4 being screwed through and projecting upwardly beyond the screw joint upper part and having a handle to perform the vertical adjustment. To establish the squeeze seal, the nut 9 is not abutted against the screw joint upper part 8, but is abutted against the upper edge of the sleeve 4.

Figure 2:
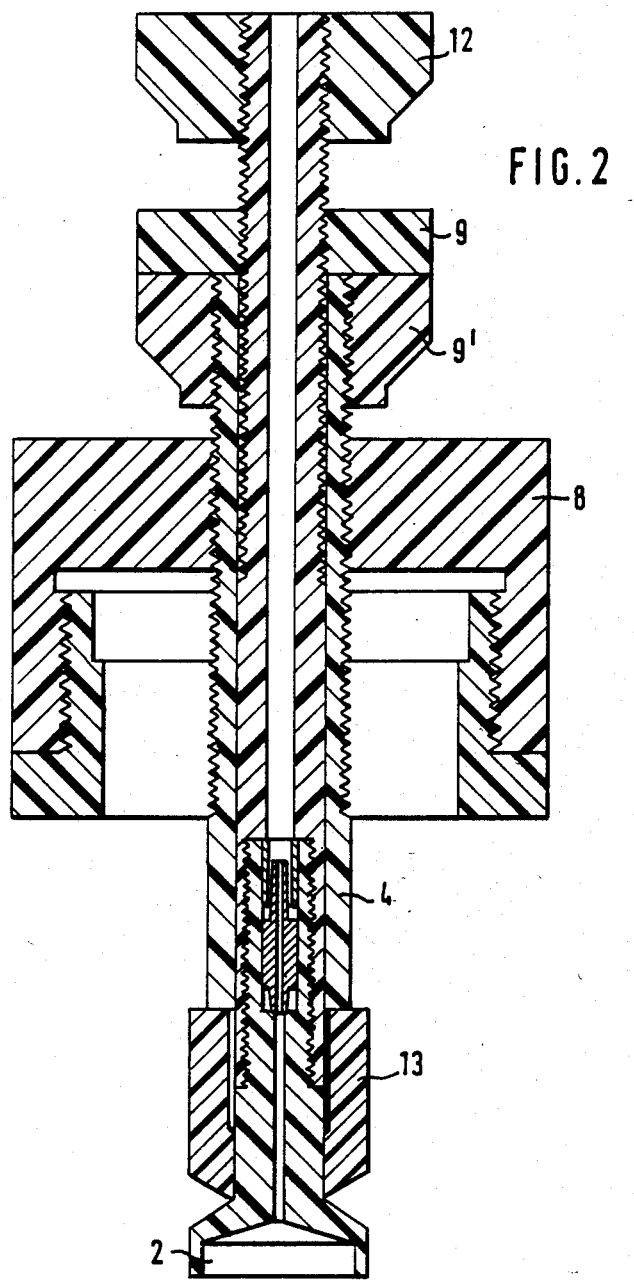
FIG. 2 is a longitudinal cross-sectional view of a vertically adjustable column.

One way of providing such vertical adjustability is shown in FIG. 2. Vertical adjustability is possible since the sleeve 4 passes displaceably through the screw joint upper part 8, and projects beyond the thread of the tube 1 or of the tube upper part 11 and since the nut 9 supports itself on the sleeve 4 in order to press the seal 6 outwardly against the glass inner wall. For adjustment of the discharge or for positioning of the frit 2, it is necessary only to loosen the nut 9 and displace the entire inset up or down. Nut 9' serves as a longitudinal adjustable flange of the sleeve 4 as well as a shoulder for the upper border of sleeve 4 to protect it from damages by turning nut 9.

Figure 3:
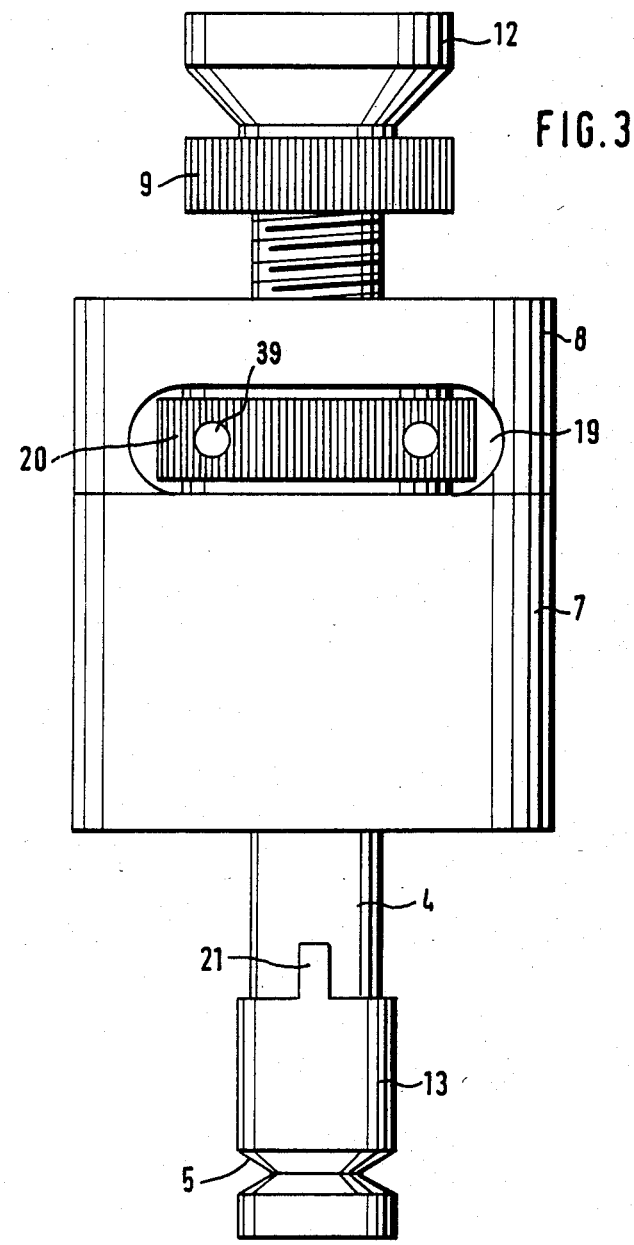
FIG. 3 is a longitudinal cross-sectional view of a vertically adjustable column.

FIG. 3 shows an embodiment having a variation of the vertical adjustment structure, in which the positioning of the frit 2 or of its recess is performed with the aid of the thread of screw joint upper part 8 and sleeve 4. In this case, the sleeve 4 is turned in the thread of the screw joint 8 and moved up or down to the extent of the thread pitch. In principle, this can take place by loosening of the nut 9 and subsequently turning the sleeve 4. Under working conditions, however, this operation involves the risk of pressure and liquid losses, for which reason the sleeve can be arranged displaceably in the screw joint upper part (FIG. 3) and an adjustment nut 20 can be arranged in the screw joint upper part 8 to operate the sleeve 4 through window 19 in the screw joint upper part. Nut 20 is supported during downward movement against the upper rim of the upper part 8 and during upward movement against the flange 16 (FIG. 1). The adjustment can be performed thereby with tightened seal. For this purpose, the adjustment nut 20 has peripherally distributed bore holes 39 into which a lever is fitted in order to assist in countering the resistance of the tightened seal. Also socket 13 is provided with an axially projecting flange 21 for positioning the socket on sleeve 4.

Figure 4:
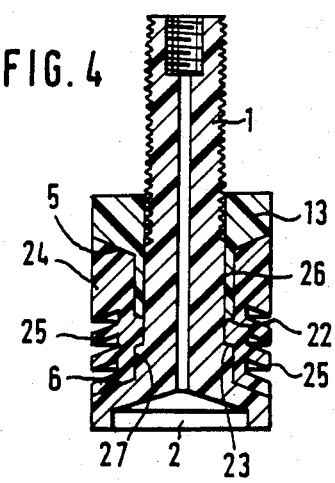
FIG. 4 is a cross-sectional view of a lip squeeze seal.

FIG. 4 shows an embodiment of the seal of plastic (PTFE) with which it is possible to dispense with a rubber O-ring. The socket 13 has a conical surface 5 and the end of the tube 1 bearing the frit recess 2 also has a conical surface 3. In addition, additional oppositely directed conical surfaces 22, 23 can be provided.

The lip seal insert 24 has sloping seal lips 25. When the seal is tightened, the conical surfaces 5 of the socket and conical surface 3 of the tube are moved toward each other and the lip seal insert 24 is compressed. As a result, the setting angle of the lips 25, which are pressed against the wall of the chromatographic column so as to seal off the column, also varies with respect to the periphery of the insert. The material thickness of the insert 24 can be varied by providing socket 13 and tube 1, respectively, with projections 26 and 27. These projections must be dimensioned depending on the elasticity or flow behavior of the material used for the lip seal insert.

Figure 5:
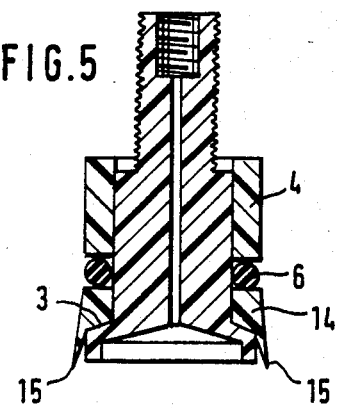
FIG. 5 is a cross-sectional view of a seal with scraper crown.

FIG. 5 shows a combined sealing device, having an O-ring 6 fitted between the sleeve 4, or between the socket 13 (not shown) and a scraper ring 14 with a crown 15. The scraper ring 14 has a counter surface matching the cone 3 and the downward jutting crown 15. Under pressure, both O-ring 6 and crown 15 widen.

One advantage of this embodiment is the possibility of being able to scrape off any material adhering to the column when the entire insert is pushed along the tube wall. Additionally, a second additional seal can be added, which improves with increasing internal pressure, so that even upon relaxation (and thus lower sliding resistance) of the clamping pressure between sleeve 4 and scraper ring 14, an easier vertical adjustment is possible without the risk of pressure loss. These features can also be added to the embodiment according to FIG. 4, so that the embodiment is especially adapted to handle the vertical adjustment according to FIG. 3.

In some cases there is a need to remove heat from the inside of the column, to heat it or to control its temperature. For these situations, as shown in FIG. 6, the screw joint is provided at both ends with outer rubber sealing rings 28 against which the cooling jacket 29 lies.

Figure 6:
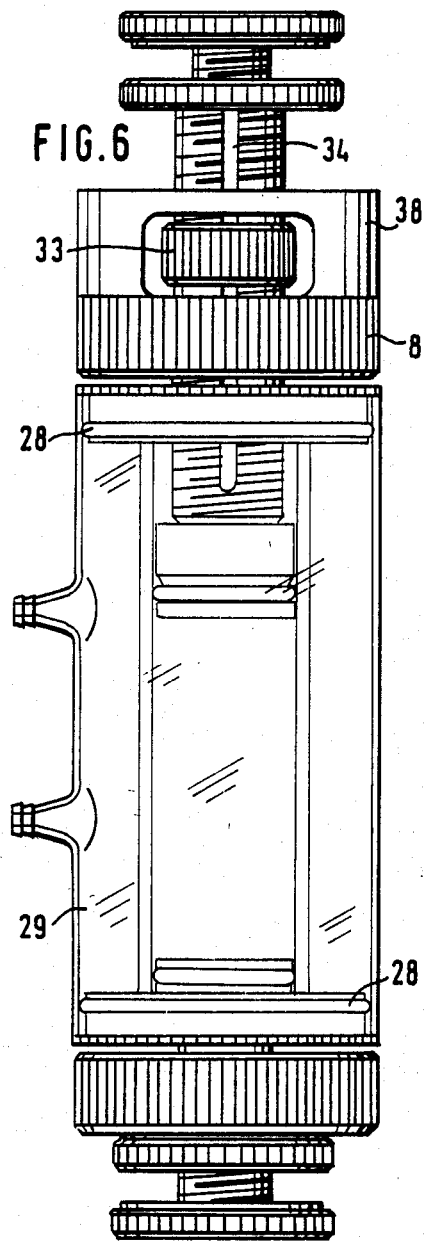
FIG. 6 is a cross-sectional view of a cooling jacket shown separately and installed on a column.

In FIG. 6, the screw joints are chosen such that only the upper one is variable in length, i.e., it is designed to be adaptable, by means of adjustment ring 33, to the bed volume. A guide groove 34 is engaged by an anti-twist device in the form of a lug or a (screwed-in) piston so that the sleeve or the entire insert can be vertically guided. The device may be accommodated in the stationary parts, such as, for example, the screw joint upper part 8, or the bracket 38 acting as a stop.

In the case of using a screw joint interacting with flanges, the inside of the column can be provided with a seal lying against the screw joint lower part so as to prevent leakage of the cooling liquid.

FIG. 7 shows another embodiment of the screw joint in which the screw joint upper parts are replaced by plates 30, 31, respectively, which are held together by tie rods 32 provided with threads and nuts 35. This embodiment is particularly adapted for handling the high pressures inside the column 36, which, for use in the embodiment, does not have any flanges for the screw joint.

The plates have central bore holes with internal threads into which the sleeve 4 engages. From the sleeve 4 projects the tube 11 with the handle 12.

FIG. 8 shows another embodiment in which the column 36 has an upper taper 37. This asymmetric shape requires different upper and lower screw joints, with the change in length, i.e., the adaptation to the bed, being performed via the upper screw joint or the knurled screw 33.

In each of the embodiments described above, a satisfactory visual inspection of the region between the frits and the transition from the frits to the separating agent bed is ensured and thus dead zones can be avoided by means of the adjustment device according to the invention, thereby considerably improving the effectiveness of the chromatography.

The present invention is suitable for use in conjunction with different glass materials and with column upper parts of a diameter from 2 to 300 mm.

The supply line can be made without any metal, since all parts coming into contact with liquid can be produced from plastic.

The adjustment path in this case can easily be up to 40 cm, and therefore, even unusual sizes can be chosen for the columns.

What is claimed is:

1. A chromatographic column, comprising:
   a column made of transparent material having an end and an inner surface;
   a tube having an upper and lower part, the lower part having a frit recess for communicating with the interior of the column and having a clamping ring comprising a surface generally facing in one axial direction;
   a sleeve surrounding the tube, the sleeve having a counterpiece comprising a surface generally facing in the opposite axial direction;
   means for supporting the sleeve on the end of the column;
   means for axially moving the tube relative to the sleeve; and
   a squeezable seal disposed around the tube and contacting the clamping ring of the tube and the counterpiece of the sleeve, the seal being adapted to move radially outwardly when the tube is moved relative to the sleeve and the seal is squeezed between the clamping ring and the counterpiece, the seal sealingly engaging the inner surface of the column as it moves radially outwardly;
   wherein the lower part of said sleeve extends below said sleeve support means to an extent sufficient to permit visual inspection of said seal.

2. A chromatographic column as claimed in claim 1, wherein the surface of the clamping ring of the tube is generally conical in shape.

3. A chromatographic column as claimed in claim 1, wherein the surface of the counterpiece of the sleeve is generally conical in shape.

4. A chromatographic column as claimed in claim 1, wherein the means for supporting the sleeve comprises a screw joint having an upper and lower part, the upper and lower part being connected to one another and the upper part being positionable on top of the end of the column.

5. A chromatographic column as claimed in claim 4, wherein the upper part of the screw joint and the sleeve are each provided with threads engageable with one another, and the sleeve passes upward through the screw joint upper part to butt against the means for axially moving the tube relative to the sleeve.

6. A chromatographic column as claimed in claim 1, wherein the means for axially moving the tube relative to the sleeve comprises a threaded portion on the outer surface of the tube and a nut threadable on the threaded portion, whereby the nut rests on the means for supporting the sleeve on the end of the column and is rotatable to axially move the tube relative to the screw.

7. A chromatographic column as claimed in claim 1, wherein the tube is split and comprises an inner screw joint and a hose clip, the hose clip being adapted to receive a supply line passed through the tube.

8. A chromatographic column as claimed in claim 1, wherein the sleeve comprises a socket on which the surface of the counterpiece is positioned.

9. A chromatographic column as claimed in claim 1, further comprising means to prevent the socket from twisting with respect to the sleeve.

10. A chromatographic column as claimed in claim 1, wherein the sleeve and the tube are provided with handles.

11. A chromatographic column as claimed in claim 1, wherein the squeezable seal comprises a rubber ring.

12. A chromatographic column as claimed in claim 1, wherein the squeezable seal comprises a plastic lip seal.

13. A chromatographic column as claimed in claim 1, further comprising a scraper ring positionable between the squeezable seal and the surface of the clamping ring of the tube, the scraper ring having a sharp edged crown for scraping the inner surface of the column.

14. A chromatographic column as claimed in claim 1, wherein the means for supporting the sleeve on the end of the column comprises a plate positionable over one axial end of the column, a plate positionable over the other axial end of the column and tie rods to interconnect the plates to one another.

15. A chromatographic column as claimed in claim 1, wherein the means for supporting the sleeve on the end of the column comprises outer sealing rings and the apparatus further comprises a cooling jacket positionable around the column, the outer sealing rings sealingly engaging the cooling jacket.

16. A chromatographic column as claimed in claim 1, wherein the means for supporting the sleeve comprises a guide groove engageable to prevent twisting of the sleeve.

* * * * *